(12) United States Patent
Duret (10) Patent No.: US 7,156,656 B2
(45) Date of Patent: Jan. 2, 2007

(54) BLEACHING DEVICE USING ELECTRO-OPTICAL AND CHEMICAL MEANS NAMELY IN THE MEDICAL AND DENTAL FIELD

(76) Inventor: Francois Duret, Chateau de Tarailhan, 11560 Fleury d'Aude (FR)

( * ) Notice: Subject to any disclaimer, the term of this patent is extended or adjusted under 35 U.S.C. 154(b) by 106 days.

(21) Appl. No.: 10/479,740

(22) PCT Filed: Sep. 24, 2003

(86) PCT No.: PCT/FR03/02814

§ 371 (c)(1),
(2), (4) Date: Jul. 19, 2004

(87) PCT Pub. No.: WO2004/028626

PCT Pub. Date: Apr. 8, 2004

(65) Prior Publication Data

US 2005/0064370 A1 Mar. 24, 2005

(51) Int. Cl.
*A61N 1/32* (2006.01)
(52) U.S. Cl. ......................... 433/32; 433/215
(58) Field of Classification Search ................ 433/215, 433/32, 25
See application file for complete search history.

(56) References Cited

U.S. PATENT DOCUMENTS

| | | | | |
|---|---|---|---|---|
| 3,215,139 A | * | 11/1965 | Dietz | .......................... 604/20 |
| 4,149,533 A | * | 4/1979 | Ishikawa et al. | ............... 604/20 |
| 4,164,214 A | * | 8/1979 | Stark et al. | .................. 600/554 |
| 4,654,794 A | * | 3/1987 | O'Brien | ....................... 433/215 |
| 4,691,718 A | * | 9/1987 | Sakuma et al. | ................ 433/32 |
| 4,952,143 A | * | 8/1990 | Becker et al. | ................ 433/32 |
| 5,372,501 A | * | 12/1994 | Shalvi | .......................... 433/32 |
| 6,167,302 A | * | 12/2000 | Millot | ......................... 604/20 |
| 6,443,732 B1 | * | 9/2002 | Lagarde | ....................... 433/224 |
| 6,497,575 B1 | * | 12/2002 | Zavitsanos et al. | ......... 433/215 |
| 6,616,451 B1 | * | 9/2003 | Rizolu et al. | ................ 433/215 |
| 6,692,250 B1 | * | 2/2004 | Decaudin et al. | ............. 433/29 |
| 6,976,841 B1 | * | 12/2005 | Osterwalder | .................. 433/29 |
| 2004/0101809 A1 | * | 5/2004 | Weiss et al. | ................. 433/224 |
| 2004/0191729 A1 | * | 9/2004 | Altshuler et al. | ........... 433/215 |

* cited by examiner

*Primary Examiner*—Ralph A. Lewis
(74) *Attorney, Agent, or Firm*—Egbert Law Offices (57) ABSTRACT

A device for bleaching a part of the human body has a wave-current generator, a plurality of electrodes and a conductive gel. The conductive gel is maintained in contact with the part of the body. An active product is cooperative with the gel so as to be activated under the presence of light or heat. A conductive circuit and a resistor define poles of the electrodes on the container of the conductive gel and the part of the body. The photosensitive bleaching product is activated by applying photonic energy of a wavelength of 400 to 500 nanometers.

16 Claims, 5 Drawing Sheets

BLEACHING DEVICE USING ELECTRO-OPTICAL AND CHEMICAL MEANS NAMELY IN THE MEDICAL AND DENTAL FIELD

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to a device for bleaching bodies ensuring their structural integrity, applicable in particular in the industrial fields for fabrics, the medical field for nails and hairs and the dental field for teeth, comprising an electrophoretic-field creator taking, directly or through an electrically active product, the active bleaching molecules towards their targets, the degraded products or those not responsible for coloration towards the outside and eventually one or several active molecules capable of reconstituting the body having been subjected to the action of the bleaching products in the body, thus decreasing any degradation in the short or medium run which could be caused by the chemical applications of the active products and the removal of the coloring molecules and eventually also including a thermal and/or photonic source activating or accelerating the activation of the products implemented for bleaching, the whole under the control of the electric or colorimetric sensor.

BACKGROUND OF THE INVENTION

Bleaching a tooth, or providing it its original natural, specific to the patient, has been an action commonly carried out in dentist's surgeries for more than 100 years and is very significant for the psychological balance of the patients.

A very good explanation for this aesthetic action was given, and constitutes a reference in this matter: the special addendum to JADA (Journal American Dental Assoc.) of April, 1997, No. 128 (addendum) pp. S1–S64 entitled "non-restorative treatment of discolored teeth, reports for an international symposium" and summarizing the congress of Chapel Hill, North Carolina of Sep. 25 and 26, 1996. An update can be found in CRA (Clinical Research Associates newsletter) Vol. 24, Apr. 4, 2000 issue or, more recently, in "Incidence of tooth sensitivity after home whitening treatment" by Jorgensen and coll. JADA, August, 2002, Vol. 133 pp. 1076–1082.

From this work can be seen that there are nowadays three important methods of bleaching used in the dentist's and medical surgeries:
  a mechanical method consisting in associating to the plaque control of teeth by mechanical means (manual and ultrasonic) abrasive polishing pastes.
  a chemical method, in general following the previous one, and consisting in applying to the tooth a product capable of removing the surface deposits as those due to tea or coffee. These products are very low-concentration carboxide- or peroxide-based products, and can be used by the patient himself at home.
  a more invasive chemical method having higher concentrations of peroxide-based product, often requiring the dental surgeon's intervention, taking into consideration the risks incurred by the patient if it does not follow its therapeutics according to the rules of the dental and medical field, and allowing to reduce the coloration of the teeth inside the dental body itself. Recently this method was modified and reduced in action in order to be usable by the patient himself at home (home kit) under cover of a periodic medical control.

Unfortunately and very quickly, both the practitioners and their patients realized that:
  the application time was very long and required the immobilization of the patient during more than 5 minutes per tooth, or 20 minutes per half arch.
  the cost of the intervention was therefore painful and prohibitive!

For this reason products were developed reacting more quickly while being activated by the light or heat. This method allows to reduce by four the time spent for the medical bleaching action.

Based on these promising results a number of products known as photosensitive were put on the market and used abundantly and successfully, associating perborate and hydrogen peroxide or peroxide carbamide activated by camphoroquinone, itself photosensitive between 400 and 500 nm. These products result from the techniques developed and introduced originally by CORCORAN and ZILLICH (1974) and by RENNEBOOG (1989). These studies highlight the role of heat and radiation brought by the halogen lamps in the activation of the bleaching products.

Thus, nowadays there exist on the market many bleaching products that are directly usable by the patient at home or that can be applied at higher concentration by the dentists. These products act directly or after activation by light or heat. They use in great majority as basic formula hydrogen peroxide at approximately 35% as described for first time by HALON in 1884.

To activate even more the reaction and to further divide by two the already considerably reduced time, it was asked to develop even more powerful lamps and it is for this purpose that the xenon-arc plasma lamp "Apollo $95^E$", patents FR 2,773,986 and FR 2,782,000, was invented and developed, which included a "bleaching" function and which supposed an action of about 30 seconds on the product placed in contact with the tooth. This product is often in the form of a gel maintained in a transparent gutter. A typical example has been sold for a long time under the name of "Apollo secrete whitening kit" (DMDS Corp. Los Angeles, USA).

Admittedly the results obtained were spectacular and many manufacturers followed this technology. However this process, even if it reduced the time considerably, had many limits.

It was indeed shown that:
  with some products the action of the lamp, therefore its effectiveness, was not only due to the photonic, but also to the thermal emissions and it is under these two effects that these products were activated.
  since the cost of these lamps is very high, the treatment remained relatively expensive,
  since these methods require high peroxide concentrations, they impeded their use by the patient at home,
  the thermal rise observed in the tooth was disproportionate compared to the activation of the product and could even be dangerous when the action was too long, it was impossible to properly control the thermal value at the very level of the tooth, to the risk of causing significant disorders in the health of dental pulp itself. Moreover, the movement even of the hand could result into changes in localization of the point of luminous or thermal impact.

by replacing the light emitted by the lamps with high thermal emission, such as the xenon-arc or halogen lamps, by lamps known as cold lamps, such as those described in FR 2,805,148 and FR 2,318,892, the heating effect was removed, which allowed the operator to increase without any risk his time of action to activate the photosensitive products, but in parallel obliged him again to a long exposure because of the elimination of the source of heat.

if a dispersed light is used over the whole arcade (for example in the form of luminous gutter), the time is again reduced, but not more than by using the high powers.

the doses implemented for treatment in the dentist's surgery (30% peroxide) as well as at the patient's home (8–10% peroxide) are extremely high compared to the aim searched for and explains the side effects observed (dental pains with the cold).

there are many repetitions because the molecules responsible for coloration are modified, even cut, but never actually removed from the site. The fact that they remain allows the recombination of the initial chemical bonds explaining the need for a re-treatment at increasingly closer intervals.

finally, the aggressive action of peroxide in contact with the gum always obliges the practitioner as well as the patient to many precautions to avoid the bums during and after the treatment.

Moreover, at no time has been solved a fundamental problem which justified the putting under monitoring of the bleaching products and in particular the peroxide by all the safety committees in the field of health of the EC and the FDA, irrespective of the degree of degradation of the tooth itself under the effect of these products, whether they are massively applied in high doses, or slowly at home by the patient himself. Do the post-operational pains result from a degradation of the tooth such as many authors affirmed? How to correct some significant decalcifications observed among patients after erroneous applied treatments?

Finally, though it is possible through known techniques to allow a faster action of the bleaching products, there is no method allowing to control, at low cost, the activation of the chemical bleaching components and to correct the degradation of the tooth following their effects.

Even more serious is what will happen with the molecules responsible for coloration. Indeed, after a treatment primarily based on the division of large colored molecules into smaller ones, the residue of this reaction remains, with the active agent, inside the dental body, which cunningly continues its action and significantly limits the penetration of fluorine or calcium.

In addition to the consequences of this steric space occupation, it can be seen well that the arrival on the site of intra-dental action of the bleaching molecule occurs by pure passive permeability, undoubtedly explaining its weak penetration, the time necessary to allow its action, the absence of a possible control of the reaction by the operator, but also a total lack of knowledge of its actual concentration in the area of action, i.e. on the molecules responsible for coloration in dental tissue.

Finally, the absence of objective and inexpensive reference to the beginning and the follow-up of the evolution of bleaching of the tooth makes its estimate perfectly subjective.

BRIEF SUMMARY OF THE INVENTION

The purpose of the present invention is to solve the above-mentioned drawbacks by providing a complete bleaching unit made up of an electrochemical system, finding its application in particular in the dental and medical fields, allowing, thanks to the creation of an electrophoretic field, a strong, fast penetration and directing the bleaching agents, their removal under the same conditions together with the molecules responsible for coloration and an effective and controlled penetration of the stabilizing agents for the apatite crystal, basic component of the tooth, such as fluorine, but also, thanks to its light-based optical system, the activation of the photosensitive bleaching products by decreasing the heat effect while increasing the photonic effect thanks to a selection of wavelength in the range of 400–500 nm and, finally, thanks to an electro-optical unit, the control of the evolution of coloration by objective spectrocolorimetry-based methods.

The purpose of the present invention is to solve these problems by providing a flexible and cheap solution usable both in a dentist's surgery and, in a simplified form, at the patient's home.

In particular it solves the many problems mentioned above, because:

by the means implemented, the device provides a natural source of energy for activating the components responsible for the bleaching, which is the ohm effect due to the passage of the electrophoretic current in a gel, the supplement brought by electric heat sources or also the addition of a photonic emission (LEDs), the cost of such a system, which allows avoiding the use of the lamps, is extremely low because an electrophoretic source is only an electric power supply. This cost becomes very low if the same power supply is used for an electric tooth-brush and the device of this invention.

the means for controlling the electrophoretic energy, provided by a simple power supply similar to a power supply for an electric tooth-brush, allows its use at the patient's home. The communication by modem allows the dentist to follow up the evolution of the treatment over the Internet.

the thermal rise caused by the device allows to activate the bleaching molecules before moving them towards the center of the tooth.

the thermal value can be fully controllable thanks to a feedback device independent from the operator.

if LEDs are used, it is not necessary to increase the time, compared to lamps with high thermal emission, because to the photonic effect is added the natural heating effect accompanying any electrophoretic current.

since LEDs are tiny, they can be placed against the operation site, avoiding the use of a lamp with fibers, which reduces the cost of the device considerably.

the doses implemented for the treatment at the dentist's as well as at home are very low for an identical effect and much higher effect at equal doses, because the active molecules are brought on the colored site and the molecules responsible for this coloration are evacuated by the electrophoretic currents.

the evacuation of the colored molecules from the tooth reduces the repetitions.

the reduction in the doses for a similar effect allows to reduce the side or undesirable effects such as the caustic action on the gum.

To this end, the present invention relates to a device for activating reactive molecules responsible for bleaching and for selectively amplifying their movements towards the inside of the tooth, of the opposite movement of the products resulting from their internal action and their replacement, by a movement also captured by the device, of the molecules stabilizing and reinforcing the structure of the tooth, the whole under the control of a system for measuring their effectiveness.

Thus the device according to the invention comprises:

a central unit allowing to control the parameters defining thermal dynamics (such as the intensity, the variation, the speed or the acceleration), photonic dynamics (such as the power and the wavelength), electrophoretic dynamics (such as the intensity, the power, the frequency, the profile and the modulation, but also a system for controlling through feedback of the action in progress or obtained), the time, the storage, the reading and the transmission of the data on various carriers a primarily electro-opto-numerical extrabuccal unit, whether included or not in the central unit and containing:

an electronic system creating a polarization field enabling us to obtain an electric, electromagnetic or electrophoretic field between the gel deposited on the tooth and the interior of the tooth and the function of which is to activate and direct a direct ion flow.

By direct action, one understands that the electric field created acts directly on the loads present (and total loads) of the molecules which are of interest to us in bleaching. Thus, there is an electric or magnetic field acting directly on the positive or negative loads of the active molecules, such as the peroxide responsible for bleaching, carrying them towards the interior of the tooth, so that they can penetrate into it quickly and strongly.

There will also be an opposite movement, whether simultaneous or not, of the whole or degraded coloring molecules, by the bleaching agents, so that they do not remain in the enamel and that they are not likely to recombine. There will finally be a last movement, whether combined or not with the bleaching agents, of the reconstituting ions of the tooth towards the interior of the enamel (for example, the negative ion fluorine at doses of 1.1 ppm).

This action can be indirect when the molecules to be moved are not electrically active. In this case, it is no longer the acting molecules (peroxide, dye and fluorine . . . ) which are pulled by the electric field, but a complementary product sensitive to the electric field and capable, because of its electric characteristics, of being pulled by this field, and, because of its chemical characteristics, of fixing itself on the acting molecules or simply of pulling them without chemical bond, but by passive carrying away, like any moving fluid is capable of carrying particles.

It should be specified that the incorporation of ions stabilizing and reinforcing the tooth fills the possible gaps resulting from the bleaching action.

According to an additional feature of the device according to the invention, it includes a device activating the photosensitive products thanks to a LED, halogen or arc light system associated with a complementary thermal system in the event cold light (LED) is used and/or when the active products are heat-sensitive. The transport of the necessary energy to the area to be bleached occurs by means of fiber when light energy is involved, by a fluid when thermal energy is involved and by wires when electric power is involved.

According to another additional feature of the device according to the invention, it includes a spectro or colorimetric sensor capable of storing and indicating, according to the comparative principle, the specific adjustments and the evolution of the coloration of the teeth. This spectrocolorimeter of elementary and inexpensive design, allows to measure, before and after treatment, the progressive change in coloration of the gel being loaded with products degraded and/or proceeding from the treated tooth released from them.

The device according to the invention also comprises an endobuccal unit containing:

a generally transparent gutter capable of containing the bleaching products such as the peroxide solutions, the dyes degraded by peroxide, and the fluorinated gel (for example). These gutters can be standard or individual for each patient and/or each type of product, in particular, in the case of indirect action.

eventually a gutter included in the first one or adaptable to it, carrying the source of lights (LEDs for example) or guiding the (halogen or plasma) light to all or part of the arch, an electrophoretic connection ensuring, according to its polarization, the fast evacuation of the components degraded under the action of the light or of the activated peroxide, and inversely, the penetration of the bleaching products or the gel loaded with reconstituent components of the tooth, eventually a thermal source, such as for example electric filaments, allowing a controlled rise in the temperature at the level of the teeth to be treated.

a gel containing the bleaching products and/or the reconstituent ions used for conducting current through the gutter from outside towards the interior of the tooth, and, eventually, another type of gel of polarization reversed or identical to the previous one, but the polarization of which has been reversed and aimed at receiving, and eventually at trapping, the coloring molecules moved out of the tooth. This gel constitutes the first pole of polarization.

The device according to the invention also comprises a polar element, a kind of handle held in the hand or in the tooth or a flexible conductive surface applied on the patient's back and allowing to bring the reversed polarity in the human body with respect to that applied in the gel of the endobuccal gutter. It is now known that this polarity will be transmitted into the dental pulp thanks to the liquids present in the human body. The human body is thus the second pole creating the electrophoretic field with the gel of the gutter.

This invention also consists in associating with a coherent aggregate of known bleaching processes the electrophoretic movements described here and in controlling their results obtained thanks to a simple monitoring system such as for example by colorimetry.

The invention thus consists in more quickly bleaching the teeth, to reduce the cost of the treatment by transporting in an active way the bleaching products very close to the molecules responsible for their coloration, in ensuring a new, unique and actual evacuation of the degraded components, and in reinforcing the apatite structure of the enamel, thanks to the active bringing in of ions such as calcium or fluorine onto the site. This new and unique design is implemented thanks to the use of electrophoretic currents combined with a supporting system of thermal or photonic activation which can result from the electrophoresis.

It is also known that a electrophoresis current causes the environmental temperature to increase during the passage of the current without another external intervention. Advantageously, the present invention thus consists in selecting a gel carrying the active bleaching ingredients capable of optimizing the well-known ohm effect accompanying the passage of the current and activating at the same time the active peroxide molecules, while avoiding the use of external heat or photonic sources.

Advantageously and according to an additional feature of the device according to the invention, if the normal rise in the temperature is not sufficient, it comprises a gutter containing a unique filament serving both as electrophoretic pole and as electric resistor allowing a thermal rise during the passage of the current, thus creating the heat source. It is known, indeed, that any passage of current is accompanied by an ohm effect. It is thus proposed here to use a polarizing wire having, in addition, a fast and consequent thermal rise during the passage of current, even if a low current, and thus allowing to reinforce the chemical and electrophoretic effect, already described, of a thermal effect activating the molecules by increasing the energy vibration, making them more reactive.

Advantageously and according to another additional feature of the device according to the invention, the electric filament will be of different size or made of different materials, according to the desired effect and, for example, and without this being restrictive, it will be of a larger size in the case of use under the control of a professional, such as a dental surgeon, in order to achieve a higher and faster thermal rise. It will be less powerful in the case of a private use at home, in order to avoid any risk.

According to another additional feature of the device according to the invention, the means for adjusting the parameters of the operation of the heat source consist of means for selecting in a memory connected to said central unit and the selection of a determined profile among several pre-stored profiles in the memory. Indeed, it is known that an optimal temperature must be obtained in order to have the best possible reaction of activation of the active ingredients of peroxide. Below or above this temperature the molecule is less active. The purpose of the memory is to optimize the time of action and the temperature obtained by natural ohm effect or by the electric resistor according to the desired degree of action. These parameters resulting from tests in laboratory and well-known to the specialists allow one to preset a priori the value of the difference in potential between the two terminals of the electrophoresis, therefore, the power and the duration of application according to the desired degree of action.

According to another additional feature of the device according to the invention, the means for adjusting the parameters of operation of the electrophoresis and the heat source are pre-stored in the memory of the central unit according to determined parameters, such as the time and the power and are adjustable by the practitioner.

Advantageously, in another case, only one parameter, such as the time, can be changed, thus avoiding any false handling and this in particular within the framework of a private use.

Advantageously, the memory connected to said central unit can be of a programmable type for recording the thermal profiles and/or the data relating to one or several adjustable parameters such as the voltage or the intensity of the current, capable of being selected.

Preferably, the device includes data-entering means, such as a keyboard with keys and/or a touch screen and/or any other data-entering means, namely remote ones, for storing in the memory the energy profile and/or data corresponding to an adjustable parameter of the memory. In the latter case, the practitioner or the patient will be able to follow up the evolution of the treatment on a screen, over the Internet or a confidential modem or any other data-transmission means.

Among the means of remote entering are the parameters for adjusting the profiles, the control of the operation of the apparatus and the detection of a possible breakdown thus allowing its remote monitoring, remote diagnosis or remote maintenance without physical intervention on the site of use.

According to an additional device of the invention, the gutter contains sensors for measuring the current or thermal or optical sensors allowing to know the evolution of the treatment before removing the gutter. Indeed it is now known that it is impossible to follow up and to know the actual state of the evolution of the bleaching treatment before the removal of the gutter. According to an additional device of this invention, this consists in providing the expert with means for knowing this evolution, thus for removing the gutter or for acting in feedback on the parameters such as the difference in potential, the intensity or the time by following the behavior of the current, because it is known that the more an electrophoresis evolves, the more the characteristics of the current also evolve. A priori the variation of the electrical current can be tested on an in vitro bench and reported in vivo in order to follow up a priori the bleaching without being obliged to remove the gutter.

According to the invention, there is an alternative to the thermal action. It is a photonic activation that can be included in the gutter and comprising a source of light and a routing of the light to the site that must receive it. This mode of action can be a compulsory alternative, because we know that some peroxides such as those present in the "ultra light" marketed by "SHOFU" are more photosensitive than heat-sensitive products. There is thus a source of light which can be halogen light, with LEDs or plasma light, such as Apollo $95^E$, or any association between them and light of which is guided by a fiber to inside the gutter. This radiation ensures, on the one hand, a photonic activation corresponding to the wavelength selected according to the absorption spectrum of the peroxide molecule and, on the other hand, a thermal activation due to the release of heat accompanying any halogen or plasma radiation.

Advantageously, this source of light is comprised of one or more light-emitting diodes (LEDs) capable of emitting in the photosensitive area of the activators of the bleaching reaction for the teeth ranging between 380 and 900 nanometers. These diodes, uniformly distributed over the gutter, for example opposite each tooth, allow the light to act at once on the complete arch.

Advantageously, these diodes use 2 sources of wavelength, one activating camphoroquinone or PPDA (470 and 430 nanometers) and/or another one producing a thermal radiation thanks to LEDs emitting in the red and the infrared (above 650 nanometers). Since the LEDs are small, they can be uniformly deposited on a die-carrier and alternately, in order to properly distribute the wavelengths over the arch. No light-conducting fiber is required, because LEDs are sufficiently small to be inserted into the patient's mouth. Only a current-supply cord connects the LEDs to the source of energy. This card will preferentially be a DC-DC supply, such as the one described in Patent FR 2,818,092. Indeed the supply mode can be the same, whether an activation reaction (peroxide) or condensation reaction (polymerization) is concerned.

Advantageously, these sources of light have a profile of the programmable type varying in time, power or wavelength, drawn or not, allowing to optimize this activation reaction.

Advantageously and according to this mode of action, there will be a uncoupling between the activation of the peroxide molecule, via the camphoroquinone, and the release of the fluorine ion. Indeed it is known that the fluorine ion can be an inhibitor in determined reactions. It is thus desirable for it to be released specifically in the electrophoretic action after the action of peroxide, i.e. after the degradation of the molecules responsible for coloration. To this end, the photonic activation of the camphoroquinone molecule and the release of fluorine will occur, according to an alternative embodiment of the invention, by two different wavelengths, one emitted by the LEDs at 470 nm for the camphoroquinone, and the other one by of LEDs the radiation of which will be different and will release the fluorine molecule at the end of the clinical bleaching operation.

Indeed, and according to the body of the invention, there is a device allowing to fill the degradations of the dental structure during the evacuation of the coloring molecules.

It is realized that the coloring molecules penetrating most deeply into the tooth, locate themselves either in spaces between crystals or in the crystal itself when the latter is not completely structured following food deficits or drug treatments during its formation (tetracycline-based antibiotics therapy, NATHOO 1997). This situation, on the one hand, makes difficult its evacuation, which justifies high concentrations of peroxide, and, on the other hand, and this is dangerous for the tooth, a degradation of the crystal itself, which justifies the restriction of the use of bleaching products or the limitation in percentage of the active agents such as hydrogen peroxide by the international health authorities. It is known for a long time that the extraction of an ion, hydroxyl, calcium or its absence, makes the hydroxyapatite crystal unstable and vulnerable. This is often leads to dental carie. That is why one recommends fluoridations of the tooth, in order to fill these ionic lacks of fluorine or calcium.

The present invention thus proposes to use the electric resistor or a complementary resistor as polarization field, allowing the active evacuation of the coloring molecules used for bleaching (peroxide), but also the creation of a reversed field, simultaneously or a posteriori, allowing a repairing ionic action as is the fluoridation of the dental body.

Indeed, it is known that fluorine is one of the determining components in allowing a restructuring of the crystal of the tooth, enamel or dentine. For this reason this ion is administered to children and adults in the event of decalcification. This ion is indeed aimed at making up the calcium deficits in the apatite crystal, allowing a stabilization of the molecular structure. This is also the reason why in the bleaching kits is included, for example, "Opalescence F1" which contains 0.11% (that is 1.1 ppm) for 5% of carbamide peroxide, but which it must nowadays diffuse in a passive, hence random way.

Advantageously, the present invention proposes to inject this ion, or a similar ion as to its action on protecting the tooth, by creating an electric field reversed with respect to the one used for the evacuation of the molecules responsible for dental coloration or of the same polarity (positive to attract fluorine, negative inside the tooth) but during evacuation and after the action of peroxide. The action can occur at the same time as the action of peroxide, since the ion used is no inhibitor. The present invention proposes to sequence the polarities according to the desired effect: action of peroxide, evacuation of the dyestuffs and reinforcement of the tooth according to the possible interrelationships of the molecules with each other. Using an electrophoretic mode not only allows to move these molecules in an active way, but also guarantees the separation of the chemical actions in order to avoid any interactive action that could be negative between the various reactions. It is the only method that allows to affirm that there is no chemical interrelationship in phases that must be separated.

To this end, it can be summarized the present invention as being an electrophoretic and chemical, incidentally thermal, bleaching device, comprising a source of energy supplying a electrophoretic current varying in polarity and the conductors of which are connected, on the one hand, to the patient's body (first pole) and, on the other hand (second pole), to a gutter containing the chemicals responsible for a bleaching treatment. These electric conductors present in the gutter allow both thermal rise by Joule effect (which can be replaced by a photonic source), but also, because of their varying electrophoretic polarization, the displacement of the molecules towards the interior of the tooth so that they are quickly and deeply active (such as the peroxide molecules or the fluorine ions, reconstituent molecules of the tooth after bleaching), and the opposite displacement towards the outside of the tooth ensuring an active evacuation of the molecules responsible for coloration. The electrophoretic field is located at the level of the tooth. One of the poles is held in the hands or on the body of the patient, this polarity is transmitted via the blood and lymphatic ways to the dental pulp, and the other pole is transmitted by the electric resistor present in the gutter.

BRIEF DESCRIPTION OF THE SEVERAL VIEWS OF THE DRAWINGS

Further aims and advantages of this invention will become clear from the following description, with reference to an embodiment given by way of an indicative and non-restrictive example. The understanding of this description will be made easier with reference to the attached drawings.

DETAILED DESCRIPTION OF THE INVENTION

As shown in these figures, the present invention relates to a bleaching device which will be of particular interest in the dental field.

Figure 1:
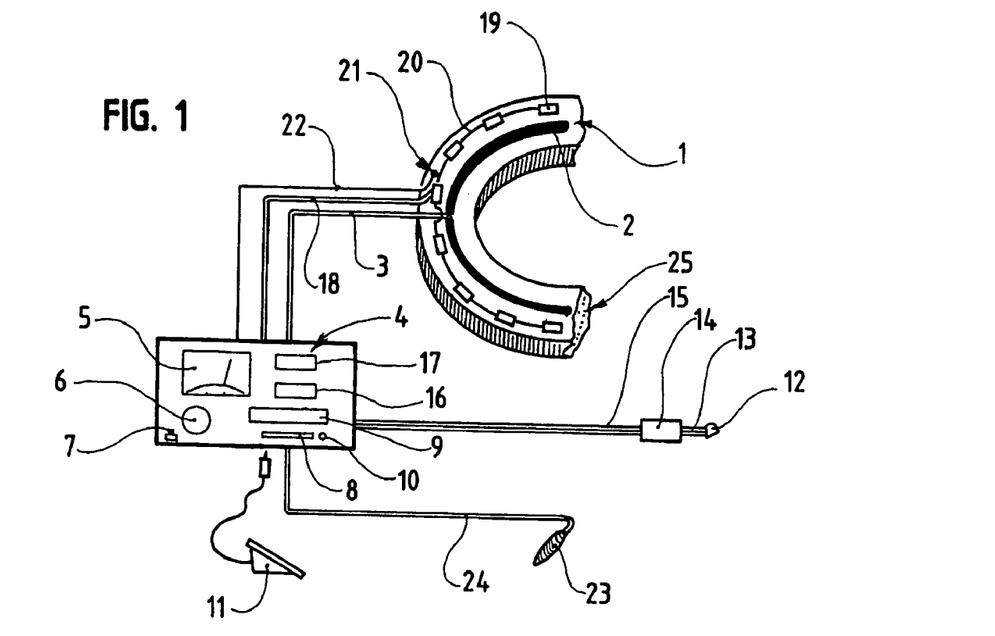
FIG. 1 shows a schematic view of a device for bleaching the teeth according to the invention.

As can be seen in FIG. 1, this device includes a standard gutter 1 with its electrophoretic resistor 2 and an array of activating LEDs 19 connected through electric connections 3 to an electronic control, monitoring and storing box 4 and with reversed polarization handle 23.

The standard gutter 1, aimed at covering the dental arch to be bleached, is provided with a electric conduction system 2 allowing the creation of an electrophoretic field, accompanied by a thermal rise, having a positive or negative polarity, and which is connected, for example by an electric lead 3, with an adjusting and control unit 4 contained in a casing, allowing to define or program the parameters of the clinical treatment (time, degree wished by the patient) and those defining the electrophoretic field (intensity, voltage . . . ). These controllable criteria on dials 5 can be modified by handling control knobs 6, remotely transmitted in a geographically off-set system and thanks to a digital link (modem . . . ) 7, stored on a diskette 8 or stored in a central unit 9. On a plug 10 can be installed a ON/OFF pedal 11 for any intervening factor such as the activating light and/or the electrophoretic field, and/or a analysis flash. The head 12 of the latter receives, thanks to a lead 13, the light emitted by reference LEDs which can e Red, Green, Blue, and in return, the information modified by the measured object, in this example a tooth. This conduction occurs through optical fibers or directly on a sensor 14 which sends the measured values to the analyzer located in unit 4. The selective startup of the spectrocolorimeter occurs, through conductive means 15, thanks to a button 16 located on the front of unit 4, and the result obtained can be seen on an alpha-numeric screen 17 located above. The startup of the heating system, thanks to the selection button 16, leads the sending of energy over a wire 18 which induces either the illumination of LEDs 19 located on the gutter 1, or the thermal rise in a resistor 20 located in the gutter 1 when the wire creating the electrophoretic field 2 is insufficient. A thermal or electric probe 21 will indicate in return the state of the electrophoresis to the central control and information unit 4. The reversed polarity with respect to that created by the resistor 2 will be transmitted to the pulp, via the blood or the lymphatic system, etc . . . , thanks to a handle 23 held in the hand and connected to the unit 4 by means of a lead 24. This polarity can be reversed automatically or by an action on button 6.

The activation of peroxides can occur thanks to the rise in temperature in a thermal resistor in common with that serving for the electrophoresis 2 or independent from the latter 20 if the selection of a different shape and/or a material can optimize any of the functions.

It should be observed in particular that the present invention is by no means limited to an electric activation of the basic components present in a bleaching gel 25 in components active on the dyestuffs and sensitive to the electrophoresis. Indeed, this activation can be carried out, according to the invention, by opto-electronic means. In this case, a resistor 2 ensures the electrophoresis, and an activating source of light is led through a lamp located in the electronic unit 4, until the bleaching gel, by an optical fiber 18, or produced directly by LEDs near the latter 19. In the latter case, the optical fiber 18 is replaced by an electric conducting wire which ensures the supply to the LEDs.

In order to control the temperature by feedback, the characteristics of the electrophoretic current and/or the light power, there is provided for a thermal, electric and/or photonic sensor 21 connected to the central control unit 4 by means of a connecting cable 22, or by a communication by waves. These sensors 21 send the necessary information to the central unit so that it controls whether the treatment is carried out according to the adjustments programmed in the central processing unit 4. This information feedback allows the periodic, even the continuous and automatic adjustment while respecting the programmed functions. It is obvious that the central unit is not compulsory for the implementation of the invention, and that a simple manual adjustment can give satisfaction in a rustic use.

If it is decided to use a gel 25 sensitive to the electrophoretic current produced by the poles 2 and 23 and a characteristic of which is to change color at the time of this activation, then of this migration, this sensor 21 can be a photosensitive cell, such as a photodiode. In this case, by applying the law of Bert Lambert, which connects the concentrations to the intensities measured by the photodiode according to the formula $Ic/Io=\log Co$, it is possible to be able to follow the evolution of the concentration of active ingredients in the tooth and the return of the degraded colored molecules. The projection of analysis light occurs at the level of head 12 of the calorimeter, whereas the reading is stored thanks to a CCD or a photodiode located in head 12 or the sensor 14.

Figures 2, 3:
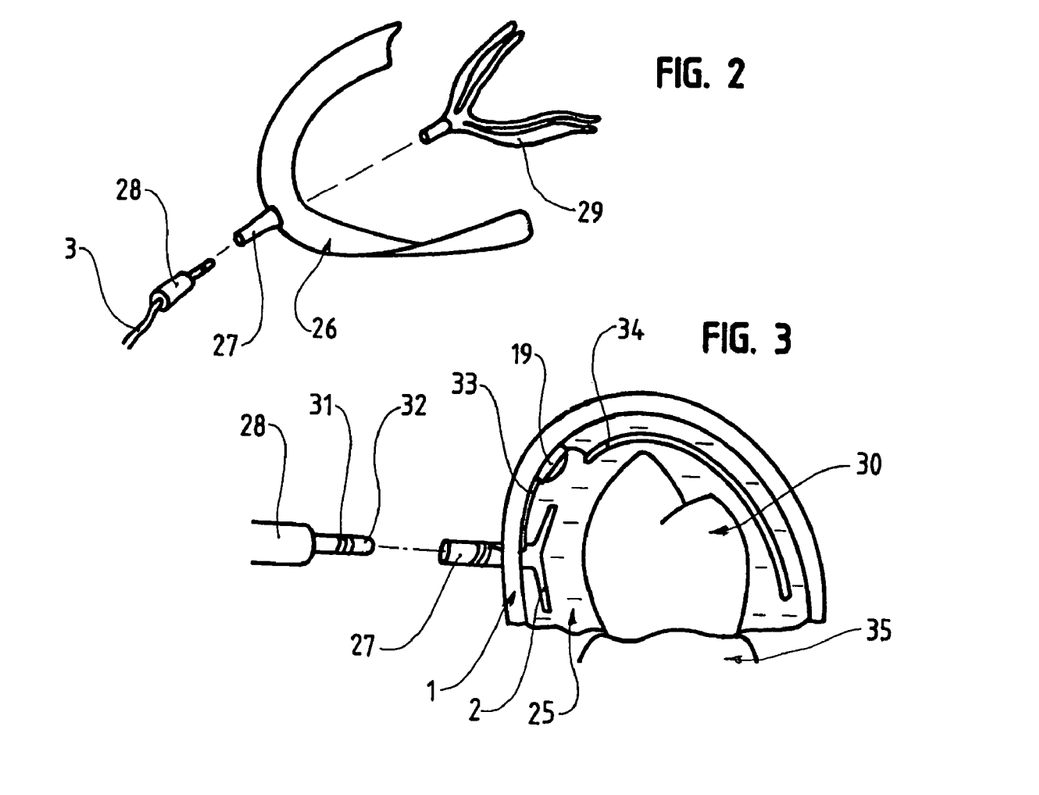
FIG. 2 shows a schematic partial and exploded view of a portion of the same device.
FIG. 3 shows a schematic cross-sectional view of a portion of the same device during a bleaching operation.

When referring now to FIG. 2, which is a schematic view of a conductive plate that can be placed against the surface of the teeth before a gutter adapted to the patient's mouth is positioned in a traditional way, it is seen that the conductive electrophoretic plate 2 can consist of a flexible lead 26 that can be placed against the surface of the teeth before a specially molded gutter adapted to the patient's mouth is positioned in a traditional way by the dentist or the prothesist. In this case, the flexible plate 26 is pressed against the teeth or pre-cast on the patient's print. According to a work perfectly known to the professionals, an anatomical gutter, i.e. specifically molded out of resin according to the shape of the patient's mouth, is then carried out. This gutter can be made out of a transparent material, in order to allow the activation of the peroxide-containing gel (or active through another chemical principle) by a light applied from outside. In this case, the electrophoretic filament will have to be pressed as close as possible to the tooth or will have to consist of a conducting material, itself transparent, such as loaded resins. The electric contribution occurs through a connector 27 and its complementary part 28 when one wishes to be able to separate the gutter 1 from the unit 4 for obvious practical reasons.

When referring to the FIG. 3, which shows a cross-sectional view of the gutter 1, one can see that the contact stop 28 is divided into two parts, one for the supply 31 and the other one for the on/off control of the heat resistor by thermal or photonic energy 34 when LEDs 19 or any other source of light are used. Since the gel 25 is conductive, the resistor 2 for creating an electrophoretic field does not need to be too large, the polarization of the field being dispersed perfectly. The light 19 or the heat resistor 34 are aimed at favoring the start of the reaction of activation of the bleaching gel 25 being in contact with the tooth 30 and somewhat with the gum 35, even though this is not desirable because of the natural aggressiveness of peroxides on soft tissues.

It will be noted that, in a non-restrictive way, the contact stop 28 is of the jack type. It can include more than one separate contact if the control through feedback or several other types of polarization must be added.

Figure 4:
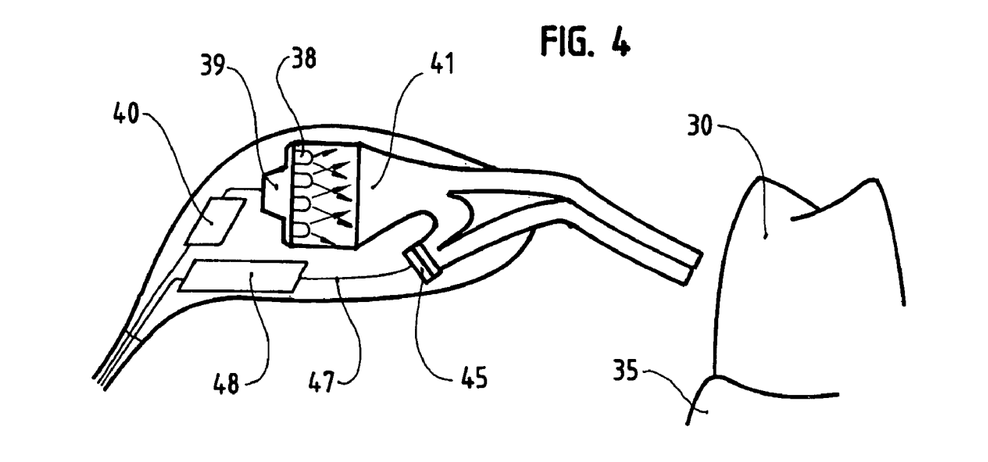
FIG. 4 shows a schematic cross-sectional partial view of another portion of the same device.
Figure 5A:
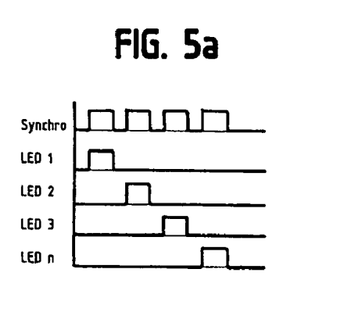
FIGS. 5a and 5b are diagrams of the representation of a cycle of analysis of the color of a tooth.
Figure 5B:
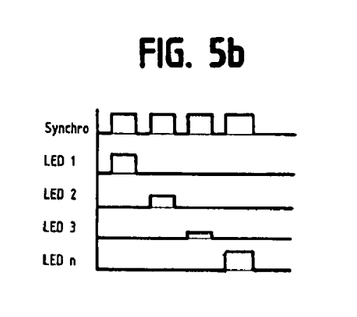

In FIG. 4 is shown an inexpensive differential colorimeter 14 being used as control unit for the effectiveness of the bleaching treatment by electrophoresis, while FIGS. 5a and 5b are diagrams A and B, respectively, of the representation of a cycle of analysis of the color of a tooth, before and after bleaching, respectively. The differential calorimeter is a very simple system based on the differential measurement of a color, before and after treatment by reflection on tooth 30.

The handling principle is as follows: a source of light is calibrated, comprised of several LEDs 38 fixed to a support evacuating the heat release 39, supplied and controlled by a DC/DC card 40. These LEDs are in a number (minimum of 2) and of varying color, but preferably Red, Green and Blue (RGB system). They emit a radiation which is taken up by an optical concentrating system 41, then led, after separation in a space in part on the tooth 30 and in part directly on a sensor 45 (generally a photodiode, a CCD or a CMOS), with or without mixing. It is possible to separate one and the same beam into two parts and to perform the measuring on two or only one sensor. It is possible also to use only one sensor 45 by shifting the measuring in the time. The information will be led from the sensor 45, via a connection 47, to a differential comparator 48 which, thanks to the analysis of the difference between the incidental beam, diagram A, and the reflected beam, diagram B, can provide a value of the color of the tooth and can compare it with the value measured before treatment.

If one took care to store in the central unit 9 the standard dental colors well-known to the specialist (Vita colors for the teeth . . . ), with the same method and the same reference (standard test), it is possible to see on the alphanumeric screen 17, and to follow the evolution, hence, the effectiveness of the treatment according to criteria recognized by the professionals. It is thus possible, according to the invention, to perform an objective measuring of the results of the treatment without being obliged to use too expensive methods.

Figures 6A, 6B:
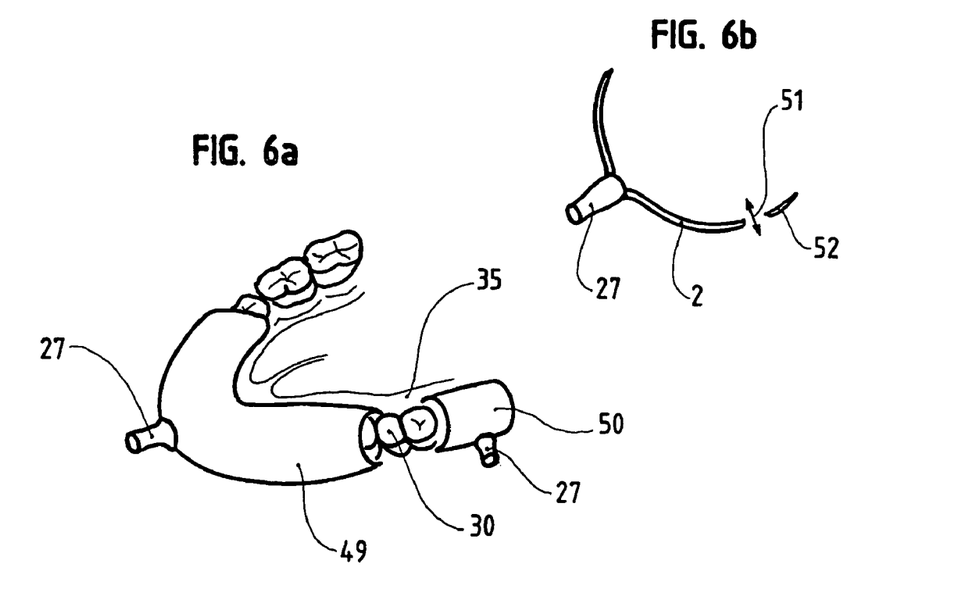
FIGS. 6a and 6b are schematic partial views of a variant of the same device.

As shown in FIG. 6a, the gutter can be only partial 49 or monodental 50, if one does not wish to treat determined teeth 30 for medical questions (pains at the collars . . . ) or if one has sensitive gums 35. The connector 27 will preferably be identical, irrespective of the type of gutter.

Likewise, and as is shown in FIG. 6b, it is possible to have a connection 27, without the gutter, simply connected to the electrophoresis lead 2 the length of which can be adapted, by making a section 51 to eliminate a portion 52, in order to limit it to some teeth.

Figure 7:
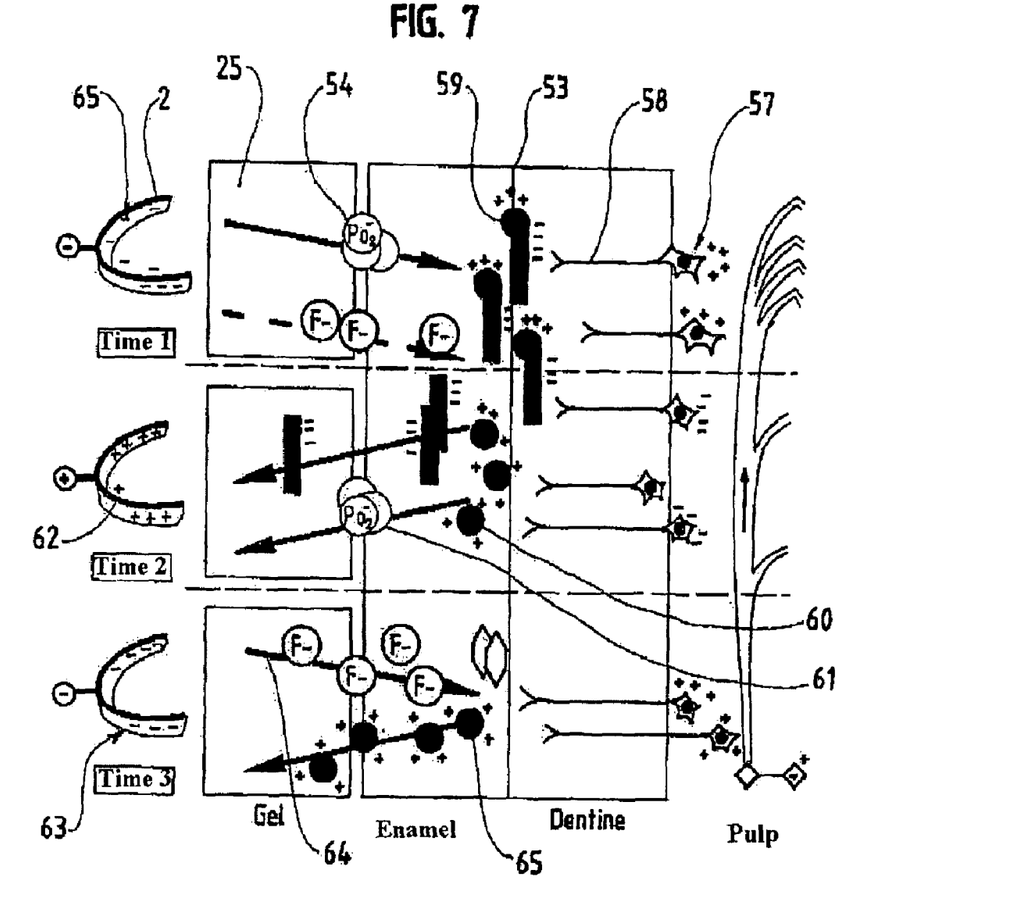
FIG. 7 is a schematic view of the various steps of the treatment implemented by the device according to the invention.

In order for the function of the device object of this invention to be well understood, in FIG. 7 has been shown the action of the electrophoretic electric fields as implemented. One can state, by way of an example, that there can exist, and this is not restrictive, three successive times using the electrophoretic bleaching currents.

In a first time, the electrophoretic current drags towards the interior of the tooth 53 the molecules rich in bleaching product, such as for example carbamide peroxide 54, present in the gel 25. If the molecules carrying the active groups are negatively charged, the polarity 55 of the resistor of the gutter is negative and the polarity of the body, for example held in the patient's hands, is positive. This polarity is transmitted to the complete tooth, via the odontoblastic cells bordering the pulp 58, mainly at the dentine/enamel interface 53 where there is often a concentration of molecules responsible for coloration 59. One will thus have an ionic movement towards the center of the tooth, pushing the active molecules against these dyestuffs. If the active molecule is not charged, one can passively drive it into the ionic movements created by additional fluids comprised of highly charged molecules.

In a second time, an reversed and unique movement, the core of the invention, is created, which is aimed at extracting from the tooth the coloring molecules 60 having been degraded by the bleaching agents 61. It is obvious the coloring molecules with an opposite polarity to that of the resistor will be extracted from the tooth. Since this polarity present in the gel 62 is the same as that of the bleaching molecules 54, the non-degraded bleaching molecules or those that have not been reacted are extracted from the tooth, in order to avoid them from continuing their action beyond the treatment and from being likely to injure the components of the tooth (which makes them hypersensitive and can even degrade them). That also allows to actually stop the process at a determined and selected time. This technique is the only one which makes controllable the bleaching of the teeth.

Finally, in a third time, but this is not restrictive in the principle of the invention, the gel resulting from the first two action times, charged with the dyestuffs and the molecules of the active product, which have been reacted or not, such as the peroxides, is removed and replaced by a fluorine-rich gel, and/or rich in any other reconstituent product of the tooth, electrically charged like the molecule carrying the active groups (peroxide). The polarity of the resistor present in the gel is again reversed 63, in order to allow, on the one hand, the penetration of the fluorine ions (or others) 64 and, on the other hand, to attract the dyestuff molecules having a reversed polarity and having been retained in the tooth during time 2.

It is obvious that, and this also falls within the principle of the invention, the fluorine can be present in the active bleaching product and migrate with the gel during time 1. The polarities are compatible. This solution has the advantage of avoiding the change of the gel in time 3, because it is then enough to reverse the polarities twice. On the other hand, this has the drawback of bringing side to side two molecules which can be incompatible, fluorine being a well-known reaction inhibitor.

Advantageously, if one wishes to accelerate the clinical procedure, one can carry out only one polarization in the direction of penetration of the active molecules, with or without fluorine, or of the exit of the degraded molecules after action of the active molecules outside the electric field. This method can be interesting if the behavior of some active molecules is disturbed during their reactions on the dyes.

There can also be programmed, according to the invention, sequences without electrophoretic current, for example, between times 1 and 2 and between times 2 and 3. This can allow to perfect determined reactions sensitive to the electrical current.

Likewise, any form of intervention on the electrophoretic current can be contemplated within the framework of the invention. Thus, one can, in a non-restrictive way:

Play on the intensity. It is shown in experiments that it is possible to significantly increase the action of the technique according to the invention by causing the intensity of the current to increase, then decrease quickly, and this by successive waves.

Cause the polarization of the poles to change, not in three times, but in an alternating way, in order to allow determined molecules to find more favorable paths into the crystal of the tooth.

Use this alternating principle, by exploiting granted time at each polarization. Times are kept as previously defined, but the polarity is reversed several times and quickly There is globally a positive or negative polarization corresponding to evoked times, but it is interrupted by reversed polarity allowing the molecules to circulate into the tooth, and eventually, to emerge from steric or electric dead ends.

Figure 8:
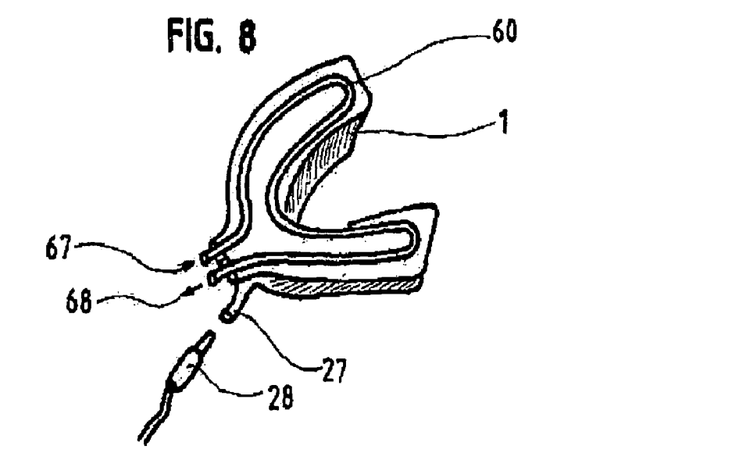
FIG. 8 is a schematic perspective view of a variant of a portion of the same device.

In FIG. 8, according to a variant, the thermal rise is brought about, not by an electric resistor, but by a circulation of water or any type of thermal vector in conduits 60 which pass through the gutter 1 by penetrating through an opening 67 and leaving through another one 68. This vector can be a liquid or a gas such as hot air. It is obvious that this mounting does not impede the addition of the electrophoretic field. In the example shown in this figure and corresponding to a possibility of implementation of the invention, the field is carried by the gutter 1 itself, which is made out of conductive material, and the connection 27–28 can be seen under the conduits of the thermal vector.

Figure 9:
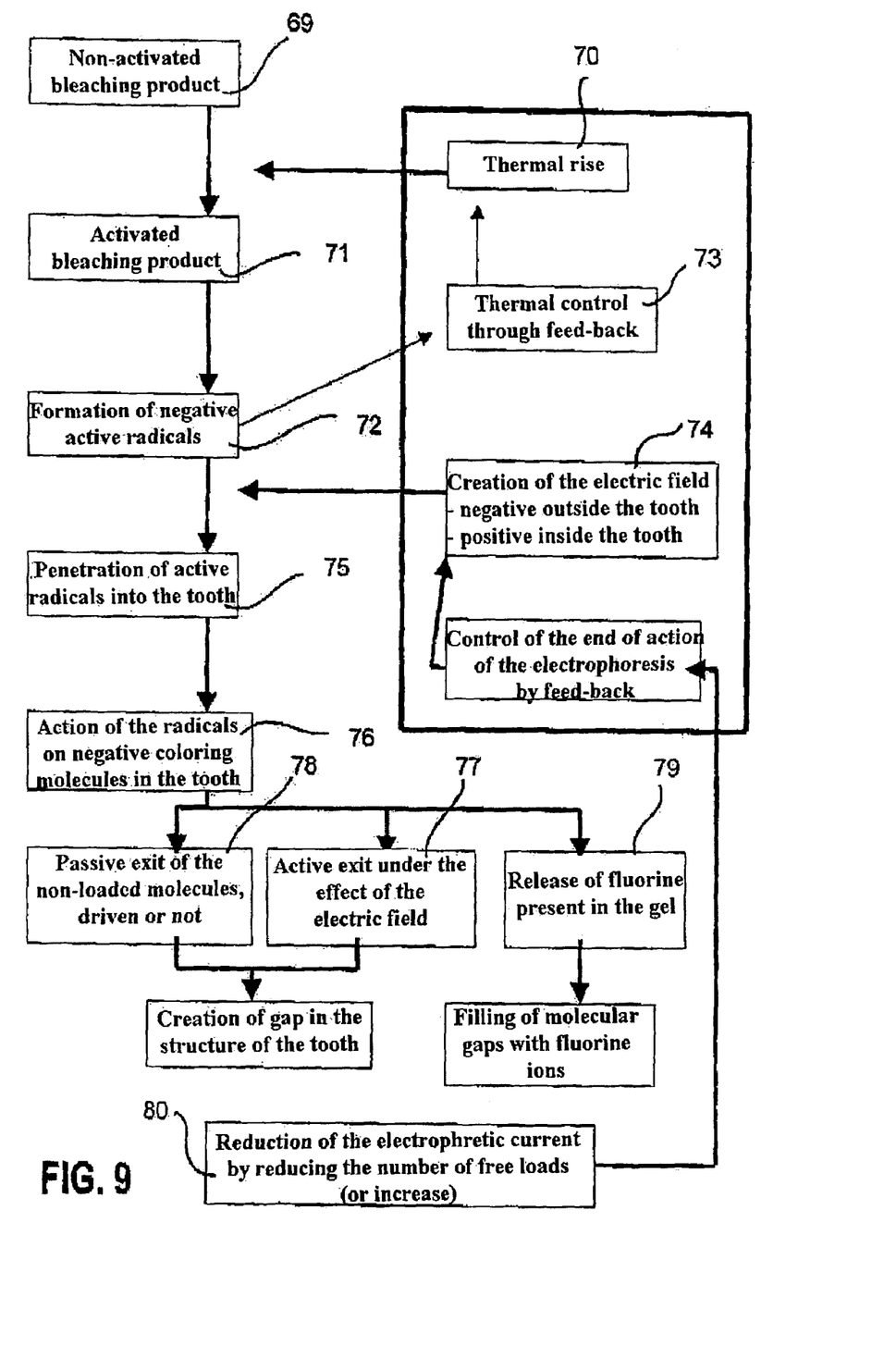
FIG. 9 is a diagram illustrating the various steps of the treatment implemented by the device according to the invention.

The diagram of FIG. 9 illustrates the successive operating steps, in the case the molecules responsible for the coloring of the tooth are of positive loaded. The non-activated product is placed in a standard gutter 69 or made to measure. The principle of activation or of acceleration of the activation of the peroxide-based molecule or other is started thanks to a thermal or photonic rise 70. The activated product 71 has a negative valence (in our example) 72. A control by feedback can limit at any time the energy contribution by directly measuring the temperature 73 and/or by following the evolution of the electrophoretic current. It is indeed at that moment that the electrophoretic field is created by placing the contact on the gutter (negative) and by asking the patient to hold the other pole (positive) 74. There is penetration of the active negative radicals into the tooth 75, attracted by the positive charges of the pulp and pushed back by the negative charges of the gutter. The peroxide molecules are then in direct contact with the molecules of dyestuff 76. This allows to significantly decrease the doses currently used, hence, to protect the tooth. Then, one reverses the polarity. The molecules of dyestuff which are degraded and positively charged leave, attracted by the negative pole of the gutter 77, together with the peroxide molecules and the not charged molecules that can be dragged passively 78. One reverses a last time the polarity, in order to allow the penetration of fluorine 79. The feedback measuring the physical characteristics of the electrophoretic current can intervene at all levels 80. the gutter 1 by penetrating through an opening 67 and leaving through another one 68.

Advantageously and according to the invention, the molecules of the active products, such as carbamide peroxide, are charged during their packaging, thus avoiding the activation phase, or are charged during the activation phase by energy means described above. These loads can be carried by a radical of the molecule independent from the peroxide radical or from the radical of any other bleaching product (reducing and/or oxidizing product).

It is also recalled that according to the invention, and to support the movements of the molecules not charged intervening in the bleaching action, it is possible to move the molecules, thanks to an indirect electrophoretic action, by dragging them by means of a loaded fluid present in the gel or added to the latter. To this end and according to the invention, a gel is provided capable of penetrating into the tooth, without chemical action on the molecules of the dyes, but very dynamic. The inversion of polarity in the tooth will cause its return out of the tooth, dragging by this second reversed movement (dynamism of the fluids) the degraded and coloring molecules.

Advantageously, the gel containing the bleaching product (for example the carbamide peroxide) and/or the tooth-reinforcing product (for example fluorine) changes color according to the concentration. For example, the movement of the peroxide groups in the tooth decreases its concentration in the gel by increasing it in the tooth. This allows, according to the invention, to follow the progression of the clinical procedure, and to stop it at a known color as the one corresponding to a good concentration of the active peroxide groups in the tooth, and to ensure a good bleaching action. The same observation can be made during the migration of fluorine (for example) or the return of the dyes.

Advantageously and according to the invention, the gel contains molecules which, in contact with the dyes, get a charge reversed to that present in the bleaching molecule (peroxide) or convert the load of the degraded dyestuff into a load reversed with respect to the peroxide. This method has the advantage of eliminating time 2 of the electrophoresis, because the loads of the dyes and those of the degraded dyes are, in this case, and according to the invention, reversed with respect to the active bleaching molecules (peroxide). They will be subjected to a reversed movement to leave the tooth and simultaneous with that of penetration of the peroxide without it being necessary to reverse the polarity. There is thus a merger of times 1 and 2, described in the example of FIG. 7 and only two times of action: times 1 and 3. If the tooth-reinforcing agent {fluorine) is present in the initial gel, it is no longer necessary to create an inversion of polarity, and one single time is then possible.

It is obvious that, according to the invention, since the charged products are very vulnerable, the activation and the polarization of the active compounds such as the carbamide peroxide occurs by mixing the basic compounds, before their introduction into the gutter.

To answer a concern for automation, one can add to the electrophoretic gel a current-measuring sensor 21 (potential difference, intensity . . . ). Indeed, it is known that during the electrophoresis there is a progressive change of the characteristics of the current involved, in particular when the ionic movement is finished, these values tend towards the infinite, it is thus easy to provide for an automatic stop, or an indication of end of cycle, hence to know whether the treatment is completed, according to pre-stored scientific criteria.

It is also obvious that, according to the invention, the thermal/electric resistor of the electrophoresis will serve for controlling by feedback the light output. The stored values allow to know whether it is necessary or not to stop the photonic action of light. It is also possible to change this light power by adjusting the parameters controlling the electric output supplied to the LEDs. The implementation of the CD-CD process as described in WO 03/068102 allows to obtain this result under the best conditions.

With this concept of control of the energy implemented in bleaching can be associated other systems commonly used at the practitioner's surgery or at the patient's home. Thus and according to the invention, the supply used at home for the electrophoresis can be shared with that used for supplying or recharging the electric toothbrushes or the portable telephones (on a journey). This duality allows to significantly reduce the price of such a device. Likewise, at the dentist's surgery, the association of this electrophoretic system with ultrasonic units or projections of abrasives (bicarbonate . . . ) allows to design a bleaching center incorporating all the apparatuses used by the specialist, without increasing its cost significantly, since the most expensive elements (supply unit), are shared by several technologies.

Advantageously, the adjustment and the control of the parameters allowing the implementation of this invention are under the control of a CPU, which is itself programmed by the specialist. There exists a chip-card system allowing to program these parameters, and it is enough for the patient to insert the card he has been given by his dentist to be sure the parameters defining the electrophoresis are in conformity with the code of practice. Finally, the device according to the invention provides the user with the possibility of regulating and adjusting the operating conditions of his apparatus in the way and where he wants, so that he is not limited, as in the past, to the blind and empirical action of peroxide without any control or follow-up.

Advantageously and according to the invention, the colorimeter 14 is associated with this control by feedback. One knows that the color of a body depends on 3 criteria referred to as L.A.B., xy and Y, RGB or the like, according to the followed theory. Using a color sensor 14 in the device allows to follow the evolution of bleaching in the course of treatment. This measuring can be performed, according to the invention, at the level of the gel which can be faded or be colored according to the contribution of coloring molecules or by reaction with the latter, as we described above. This allows to know whether one must stop or not the application, and avoids having to proceed in an empirical way. This also avoids stopping the action before the end of the treatment and allows to limit the expenses incurred. Likewise, this system of measurement can be carried out on the tooth, before and after treatment, thus allowing the practitioner to show to his patient the evolution of bleaching. To this end, a special sensor 12 comprised of the color measurer described above in FIG. 4 has been developed, the end of which can:

either be integrated into the gel, or be placed on the tooth.

Figure 10:
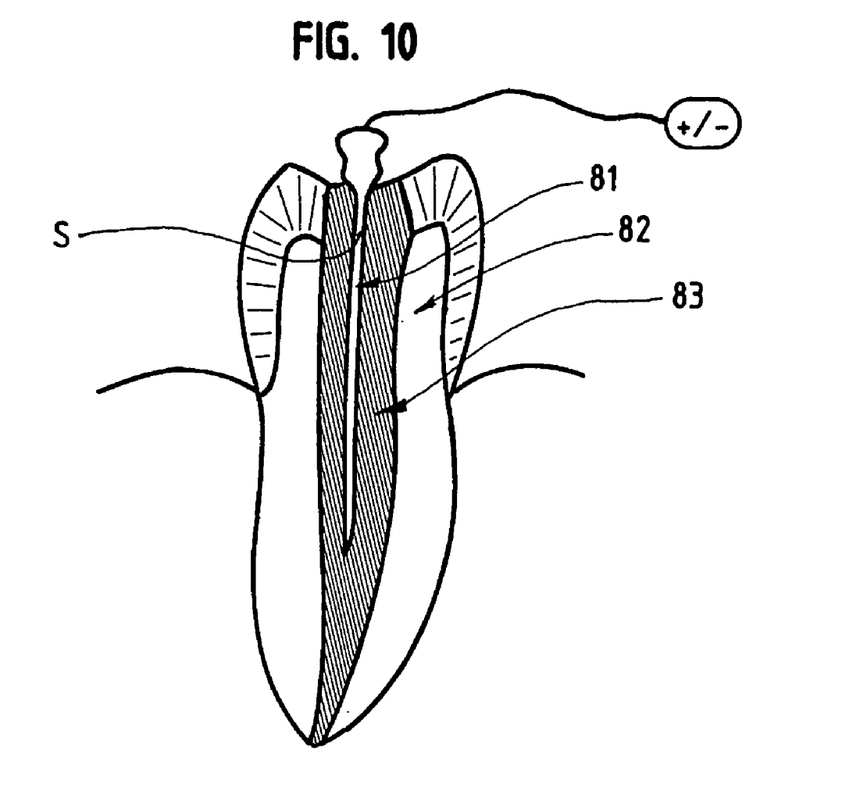
FIG. 10 is a schematic vertical cross-sectional view of a tooth devitalized during its treatment by means of the device according to the invention.
Figure 11:
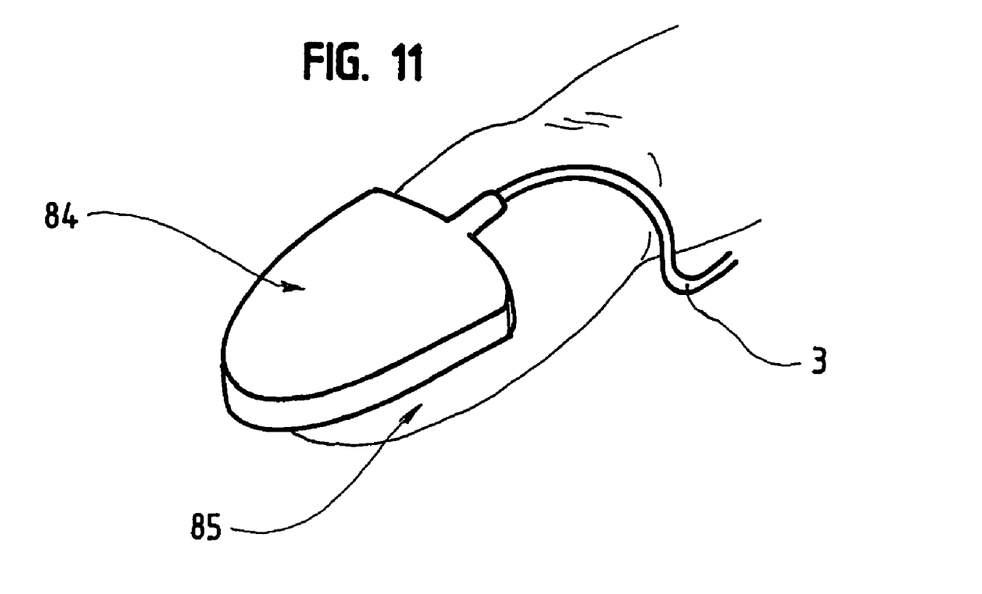
FIG. 11 is a schematic partial view of a particular embodiment of the device according to the invention, adapted for treating nails.

It remains however a fact that most bleaching devices cannot act on devitalized teeth or can so with the help of high concentrations or with the use of specific products such as borates. This would also apply to this invention if a solution were not proposed, since, after the pulp and the blood circulation have been removed, there can no longer be an electric conduction of reversed polarity with respect to that of the gel inside the tooth. The present invention provides an alternative especially developed for the devitalized teeth. Advantageously and according to the invention, as can be seen in FIG. 10, the pole held in the patient's hand or placed against his body, is replaced by or coupled (in series) to a probe S that can be inserted into the dental channel 81 of the previously drilled devitalized tooth 82. A conductive gel 83 is placed in the channel to replace the dental pulp which does no longer exist, after care has been taken to humidify the tooth. The function of conduction of the second pole is thus again created, even in absence of pulp.

Advantageously and still according to the invention, this gel contains active bleaching components and fluorine, as we observed in the external gel, but of reversed polarity, so that they are attracted towards the gel of this external gutter. One creates a second movement of active molecules reversed with respect to that of the gutter of the external pole. If there are no active molecules of reversed polarity, it is enough to repeat the operation in a sequential way: external bleaching, then, internal bleaching etc . . . by using the same gel and the same polarity (as described in FIG. 7, but with an inversion of polarity, according to whether the active gel is inside or outside the tooth.

This extension of the invention has the advantage of allowing a technique for bleaching devitalized teeth, which is very important because they are often the most colored teeth. This has also the advantage of increasing even more significantly the action of the products since they have moved electrophoretically towards the colored molecules of the inside and the interior of the tooth. With this double internal and external action is associated an action of extirpation of the molecules of dyestuff on both sides. In this case, and in order to understand the mechanism of bleaching from the internal pole, it is enough to reverse times 2 and 3 of FIG. 7.

When referring now to FIG. 7, one can see that the invention is not limited to the bleaching of teeth, but that it also finds an application to the treatment of other parts of the body such as tissues or hairs, and in this case nails. This figure thus shows a gel-supporting means 84, adapted to the end of a finger 85, and covering the nail, not visible, of the latter.

It can be seen from the preceding description that the present invention perfectly solves the problems set forth in that it provides a real answer for optimizing the bleaching of the teeth and the protection of the dental organ. From this description also results that it allows to solve fundamental problems, such as the control of the clinical action, which no other method has provided so far.

It is obvious that the invention is not limited to the only mode of implementation of this process, nor to the only embodiments of the device for the implementation of this process, described above by way of examples; it embraces, on the contrary, all the variants of implementation and embodiment. Thus, it would be possible, in particular, to bleach objects other than parts of the human body, such as, for example, statues or fabrics. It is also possible to contemplate a type of industrial washing based on the present invention and ensuring the movements of penetration of the cleaning body or of extirpation of the molecules responsible for coloring by electrophoresis.

I claim:

1. A bleaching device for bleaching parts of the body, the device comprising:

an electrophoretic wave current generator with a varying modulation;

a means for transmitting current from the wave-current generator to the part of the body to be bleached;

a means for creating a non-traumatizing field through the part of the body to be bleached, said means for creating comprising a plurality of electrodes and a conductive gel, the field being selected from a group consisting of electric, electrophoretic and electromagnetic;

a means for containing said conductive gel in contact with said plurality of electrodes and the part of the body to be bleached so as to cause a continuous field;

an active product suitable for bleaching which is sensitive to the current; and means for activating said product, said means for activating being selected from a group consisting of heat and light, said means for containing said conductive gel having a conduction circuit and a resistor so as to define a first pole in said means for containing said conductive gel and a second pole in contact with the part of the body.

2. The device of claim 1, further comprising:

a central unit means for controlling and storing and monitoring parameters of the wave-current generator.

3. The device of claim 1, said means for containing said conductive gel comprising: a gel molded onto the part of the body.

4. The device of claim 1, said second pole in contact with the body being placed in a tube containing an electrophoretic bleaching gel as a root of a devitalized tooth.

5. The device of claim 1, said means for activating comprising:
 a photonic activator suitable for activating said product.

6. The device of claim 1, said means for containing said conductive gel comprising:
 a source of light selected from a group consisting of halogen light, arc light and LED light transmitted by an optical fiber.

7. The device of claim 1, said means for containing said conductive gel incorporating light-emitting diodes generating a source of light.

8. The device of claim 1, said means for containing said conductive gel comprising:
 a means for controlling an electrical or thermal evolution of the gel, said means for controlling comprising a sensor.

9. The device of claim 8, said means for controlling comprising:
 a colorimeter having a light generation and a differential analyzer.

10. The device of claim 1, said generator having a varying modulation in tension, frequency and amplitude.

11. The device of claim 1, said conductive gel containing electrically-charged molecules which are suitable for moving through said gel toward the part of the body under action of the current.

12. The device according to claim 1, wherein said conductive gel contains electrically charged molecules responsible for action of reinforcement of the body to be treated, the molecules moving through the gel towards the body to be treated under the action of the current used and compensating for possible degradations caused by bleaching action.

13. The device according to claim 1, wherein said conductive gel is electrically charged, the gel allowing molecules to be dragged and moved passively towards the body under action of displacement of the gel by movement of the gel, said molecules being responsible for bleaching or reinforcing action, said molecules not being electrically charged.

14. The device of claim 1, further comprising:
 a button means for reversing a polarity of said first pole and said second pole of said means for containing said conductive gel.

15. The device of claim 1, said means for activating said product comprising:
 an electric resistor connected to a photonic emitter or a circulating fluid.

16. The device of claim 1, said conductive gel being color-changeable relative to the current applied thereto.

* * * * *